(12) United States Patent
Kaplan et al.

(10) Patent No.: US 9,617,343 B2
(45) Date of Patent: *Apr. 11, 2017

(54) METHODS AND COMPOSITIONS FOR TREATING LUPUS

(75) Inventors: Johanne M. Kaplan, Sherborn, MA (US); Bruce L. Roberts, Southborough, MA (US); William M. Siders, Franklin, MA (US)

(73) Assignee: GENZYME CORPORATION, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/320,001

(22) PCT Filed: May 13, 2010

(86) PCT No.: PCT/US2010/034741
§ 371 (c)(1),
(2), (4) Date: Nov. 10, 2011

(87) PCT Pub. No.: WO2010/132683
PCT Pub. Date: Nov. 18, 2010

(65) Prior Publication Data
US 2012/0070408 A1    Mar. 22, 2012

Related U.S. Application Data

(60) Provisional application No. 61/177,924, filed on May 13, 2009.

(51) Int. Cl.
| | | |
|---|---|---|
| *A61K 39/395* | (2006.01) | |
| *A61K 38/18* | (2006.01) | |
| *A61K 38/20* | (2006.01) | |
| *A61K 38/21* | (2006.01) | |
| *A61P 13/02* | (2006.01) | |
| *A61P 37/04* | (2006.01) | |
| *C07K 16/28* | (2006.01) | |
| *A61K 39/00* | (2006.01) | |

(52) U.S. Cl.
CPC .... *C07K 16/2893* (2013.01); *A61K 2039/505* (2013.01)

(58) Field of Classification Search
None
See application file for complete search history.

(56) References Cited

U.S. PATENT DOCUMENTS

| | | |
|---|---|---|
| 5,545,404 A | 8/1996 | Page |
| 7,119,248 B1 | 10/2006 | Rajewsky et al. |
| 7,465,790 B2 | 12/2008 | Waldmann et al. |
| 2004/0219156 A1 | 11/2004 | Goldenberg et al. |
| 2005/0118172 A1 | 6/2005 | Hale et al. |
| 2005/0191632 A1* | 9/2005 | Byrd et al. ............... 435/6 |
| 2005/0260204 A1 | 11/2005 | Allan et al. |
| 2006/0228351 A1 | 10/2006 | Masuyama et al. |
| 2006/0292644 A1* | 12/2006 | Trakht et al. ............... 435/7.23 |
| 2008/0038223 A1 | 2/2008 | Hunter et al. |
| 2014/0341910 A1* | 11/2014 | Roberts et al. ........... 424/139.1 |
| 2016/0024219 A1 | 1/2016 | Qiu et al. |

FOREIGN PATENT DOCUMENTS

| | | |
|---|---|---|
| EP | 1618891 A1 | 1/2006 |
| WO | WO 92/07084 | 4/1992 |
| WO | WO 2004/087210 | 10/2004 |
| WO | WO 2005/042581 | 5/2005 |
| WO | 2007125362 | 8/2007 |
| WO | WO 2007/121233 | 10/2007 |
| WO | WO-2007140457 | * 12/2007 |
| WO | WO 2008/108776 | 9/2008 |
| WO | WO 2008/140484 | 11/2008 |
| WO | WO 2010/132659 | 11/2010 |

OTHER PUBLICATIONS

U. S. Appl. No. 13/319,991, filed Nov. 10, 2011.*
U. S. Appl. No. 13/320,019, filed Nov. 10, 2011.*
Leandro et al. An open study of B lymphocyte depletion in systemic lupus erythematosus. Arthritis Rheum. Oct. 2002;46(10):2673-7.*
Pisoni et al. Mycophenolate mofetil in systemic lupus erythematosus: efficacy and tolerability in 86 patients. J Rheumatol. Jun. 2005;32(6):1047-52.*
U.S. Appl. No. 14/091,083, filed Nov. 26, 2013.*
Bloom et al., "CDf$^+$ CD25$^+$ FoxP3$^+$ regulatory T cells increase de novo in kidney transplant patients after immunodepletion with Campath-1H," Am. J. Transplant, 8(4):793-802 (2008).
Cohen et al., "Treatment of refractory autoimmune diseases with ablative immunotherapy," Autoimmun. Rev., 3(2):21-29 (2004).
Hu et al., "Investigation of the mechanism of action of alemtuzumab in a human CD52 transgenic mouse model," Immunology, 128:260-270 (2009).
Li et al., "B cell depletion with anti-CD79 mAbs ameliorates autoimmune disease in MRL/lpr mice." J. Immunol., 181(5):2961-2972 (2008).
Loh et al., "Development of a secondary autoimmune disorder after hematopoietic stem cell transplantation for autoimmune diseases: role of conditioning regimen used," Blood, 109(6):2643-2648 (2007).
Moreton et al., "Alemtuzumab therapy in B-cell lymphoproliferative disorders," Semin. Oncol., 30(4):493-501 (2003).
Pascual et al., "Alemtuzumab induction and recurrence of glomerular disease after kidney transplantation," Transplantation, 83(11):1429-1434 (2007).
Pugh-Bernard et al., "B cell receptor signaling in human systemic lupus erythematosus," Curr. Opin. Rheumatol, 18(5):451-455 (2006).
Singh et al., "Rapamycin promotes the enrichment of CD4$^+$CD25$^{hi}$FoxP3$^+$T regulatory cells from naïve CD4($^+$) regulatory T-cells of baboon that suppress anti porcine xenogenic response in vitro," Transplant Proc., 41(1):418-421 (2009).
Suen et al., "Altered homeostasis of CD4($^+$) FoxP3($^+$) regulatory T-cell subpopulations in systemic lupus erythematosus," Immunology, 127(2):196-205 (2008).

(Continued)

Primary Examiner — David Romeo
(74) Attorney, Agent, or Firm — Steptoe & Johnson LLP; Z. Ying Li; Wyan-Ching M. Lee

(57) ABSTRACT

The invention provides methods of treating lupus in a patient with an anti-CD52 antibody. Also includes are methods of increasing infiltration of regulatory T cells to affected sides of the patient's body, methods of reducing urine protein and/or albumin levels and methods of depleting lymphocytes to alleviate lupus symptoms.

17 Claims, 25 Drawing Sheets

(56) References Cited

OTHER PUBLICATIONS

Yoshio et al., "Expression of CD52 on peripheral blood T lymphocytes closely correlates with disease activity in patients with systemic lupus erythematosus (SLE)," Arthritis and Rheumatism, 54(9):S459-S459 (2006).
Bonelli et al., "Phenotypic and functional analysis of CD4+CD25-Foxp3+ cells in patients with systemic lupus erythematosus," J. Immunol., 182:1689-1695 (2009).
Gregersen et al., "B-cell depletion in the treatment of lupus nephritis," Nature, 8:505-514 (2012).
Kuhn et al., "CD4+CD25+ regulatory T cells in human lupus erythematosus," Arch. Dermatol. Res., 301:71-81 (2009).
Noris et al., "Regulatory T cells and T cell depletion: role of immunosuppressive drugs," J. Am. Soc. Nephrol., 18:1007-1018 (2007).
Sharabi et al., "Harnessing regulatory T cells for the therapy of lupus and other autoimmune diseases," Immunotherapy, 1:385-401 (2009).
Zhang et al., "Reduction of forkhead box P3 levels in CD4+CD25$^{high}$ T cells in patients with new-onset systemic lupus erythematosus," Clin. Exp. Immunol., 153:182-187 (2008).
Baráth et al., "The severity of systemic lupus erythematosus negatively correlates with the increasing number of CD4+CD25$^{high}$ FoxP3+ regulatory T cells during repeated plasmapheresis treatments of patients," Autoimmunity, 40:521-528 (2007).
"Anti-Mouse CAMPATH-1/CD52," MBL International Corporation, Monoclonal Antibody, D204-3 & "PE labeled Mouse CD52/CAMPATH-1," MBL International Corporation, Monoclonal Antibody, D204-5.
Kubota et al., "Identification and gene cloning of a new phosphatidylinositol-linked antigen expressed on mature lymphocytes. Down-regulation by lymphocyte activation," J Immunol., 145:3924-3931 (1990).
Watanabe et al., "CD52 is a novel costimulatory molecule for induction of CD4+ regulatory T cells," Clinical Immunology, 120:247-259 (2006).
Krasnova, "Kidney affection upon the systemic lupus erythematosus: modern conceptions about pathogenesis, clinical picture, treatment approaches," Modern Rheumatology, 3:18-21 (2008) (Russian language, partially English).
Rashedi et al., "Autoimmunity and Apoptosis—Therapeutic Implications," Curr. Med. Chem., 14:3139-3151 (2007).
Richard, Allogeneic Stem Cell Transplantation in Systemic Lupus Erythematosus, ClinicalTrials.gov Identifier NCT00278590, https://clinicaltrials.gov/ct2/show/NCT00278590?term=Systemic+Lupus+Erythematosus+and+Campath&rank=3 (2006).
Duke University, Nonmyeloablative Allo Stem Cell Transplant for Severe Autoimmune Diseases, ClinicalTrials.gov Identifier NCT00849745, https://clinicaltrials.gov/ct/2/show/NCT00849745?term=alemtuzumab&rank=254 (2009).
Cairo, Reduced Intensity Transplant in Medically Refractory Systemic Lupus Erythematosus (SLE) and Systemic Sclerosis (SSc), ClinicalTrials.gov Identifier NCT00684255, https://clinicaltrials.gov/ct2/show/study/NCT00684255?term=alemtuzumab&rank=195 (2008).
Ribeiro et al., "The Activation Sequence of Thrombospondin-1 Interacts with the Latency-associated Peptide to Regulate Activation of Latent Transforming Growth Factor-Beta," J. Biol. Chem. 274(19):13586-13593 (1999).

* cited by examiner

Square: Mice that succumbed during the course of the study
Circle: Mice that survived until the end of the study

US 9,617,343 B2

METHODS AND COMPOSITIONS FOR TREATING LUPUS

This application is a national stage application under 35 U.S.C. §371 of International Application PCT/US2010/034741 (now pending), filed May 13, 2010, which claims priority from U.S. Provisional Application 61/177,924, filed May 13, 2009. The contents of the foregoing priority applications are incorporated by reference herein in their entirety.

A Sequence Listing associated with this application is being submitted electronically via EFS-Web in text format, and is hereby incorporated by reference into the specification. The name of the text file containing the Sequence Listing is 001662_0020_301_Sequence_Listing.txt. The text file, created on Nov. 10, 2011, is 1,102 bytes in size.

BACKGROUND OF THE INVENTION

Lupus is an autoimmune disease that can affect many parts of the body, such as blood, central nervous system (CNS), heart, liver, joints, kidneys, lungs, skin, intestinal tract, and vasculature. Inflammations are commonly observed in the tissues or organs affected by lupus. Symptoms of lupus include abnormal blood panels, arthralgias, atherosclerosis, CNS disorders, infections, joint pain, malaise, rashes, ulcers, nephritis, cardiovascular disease, and the production of autoantibodies. Lupus has manifestations including systemic lupus erythematosus, lupus nephritis, cutaneous lupus erythematosus, CNS lupus, cardiovascular manifestations, pulmonary manifestations, hepatic manifestations, haematological manifestations, gastrointestinal manifestations, musculoskeletal manifestations, neonatal lupus erythematosus, childhood systemic lupus erythematosus, drug-induced lupus erythematosus, anti-phospholipid syndrome, and complement deficiency syndromes resulting in lupus manifestations. See, e.g., Robert G. Lahita, Editor, *Systemic Lupus Erythematosus,* 4th Ed., Elsevier Academic Press, 2004. In the United States, approximately 1.5-2 million people suffer from lupus. 90% of these lupus patients are female. At present, lupus is typically treated with corticosteroids and immunosuppressants. There is an urgent need for improved therapeutic methods and compositions for treatment of lupus.

SUMMARY OF THE INVENTION

We have invented new and useful methods and compositions for treatment of lupus with anti-CD52 antibodies (e.g., alemtuzumab). In some embodiments, antibodies that significantly deplete lymphocytes are used. In other embodiments, methods, antibodies that do not significantly deplete lymphocytes can also be used.

In one aspect, the invention provides methods of increasing FoxP3+ (e.g., CD4+CD25+FoxP3+) regulatory T cells in a patient with lupus, comprising administering to the patient a therapeutically effective amount of an anti-CD52 antibody. In some embodiments, the methods further comprises administering to the patient an agent that stimulates said regulatory T cells, for example, rapamycin, TGF-β (active or latent TGF-β1, TGF-β2, TGF-β3, TGF-β4, or TGF-β5), IL-10, IL-4, IFN-α, vitamin D3, dexamethasone, or mycophenolate mofetil. The regulatory T cells may infiltrate to a site of inflammation in the lupus patient, for example, blood, the central nervous system (CNS), heart, liver, joint, kidney, lung, skin, intestinal tract, or vasculature.

In another aspect, the invention provides methods of reducing urine protein and/or albumin level in a patient with lupus, comprising administering to the patient a therapeutically effective amount of an anti-CD52 antibody.

In another aspect, the invention also provides methods of depleting lymphocytes (e.g., B cells and T cells) in a patient with lupus, comprising administering to the patient a therapeutically effective amount of an anti-CD52 antibody.

In another aspect, the invention also provides methods of treating a patient in need thereof (e.g., a lupus patient), comprising administering to the patient a therapeutically effective amount of an anti-CD52 antibody in combination with at least a second compound. The second compound is typically one that is used to treat lupus, for example, a standard-of-care or experimental treatment.

The methods of this invention can be used to treat a patient who has one or more manifestations of lupus, including, without limitation, systemic lupus erythematosus, lupus nephritis, cutaneous lupus erythematosus, central nervous system (CNS) lupus, cardiovascular manifestations, pulmonary manifestations, hepatic manifestations, haematological manifestations, gastrointestinal manifestations, musculoskeletal manifestations, neonatal lupus erythematosus, childhood systemic lupus erythematosus, drug-induced lupus erythematosus, anti-phospholipid syndrome, or complement deficiency syndromes resulting in lupus manifestations.

In the combination therapy methods of this invention, the anti-CD52 antibody and the additional therapeutic agents can be administered in any order as appropriate for the patient. The anti-CD52 antibody and the additional agent(s) can be administered concurrently or sequentially, or both. For example, the additional agent(s) can be administered before or after the anti-CD52 therapy. Also provided in this invention are kits useful for such combination therapy.

In some embodiments, the patient is a human patient, and the anti-CD52 antibody is directed against human CD52. In those embodiments, it may be preferred that the anti-CD52 antibody is a human antibody, a humanized antibody, or a chimeric antibody with a human Fc portion.

The invention also provides uses of the anti-CD52 antibody to manufacture medicament useful for the treatment methods of this invention.

BRIEF DESCRIPTION OF THE FIGURES

FIGS. 2A-2E show that anti-mouse CD52-treated mice displayed urine protein levels comparable to those of mice in the positive control cyclophosphamide-treated group, whereas control rat IgG-treated mice showed urine protein levels comparable to those of vehicle control (PBS)-treated mice. FIG. 2F shows that, by the end of the study, only 38% of the anti-mouse CD52 antibody-treated mice and 20% of the cyclophosphamide-treated mice reached severe proteinuria (>500 mg/dL/day), compared to 67% of the rat IgG and 60% of the vehicle treated mice.

FIGS. 3A-3F show that urine albumin levels in the anti-CD52 antibody-treated mice were lower than those seen in the vehicle (PBS) and control rat IgG-treated mice. FIG. 3G shows that only 50% of the anti-CD52 antibody-treated mice developed significant albuminuria (>40 mg/dL/day) compared to 80% of the vehicle-treated and 89% of the rat IgG-treated mice by the end of the study.

DETAILED DESCRIPTION OF THE INVENTION

Figure 1A:
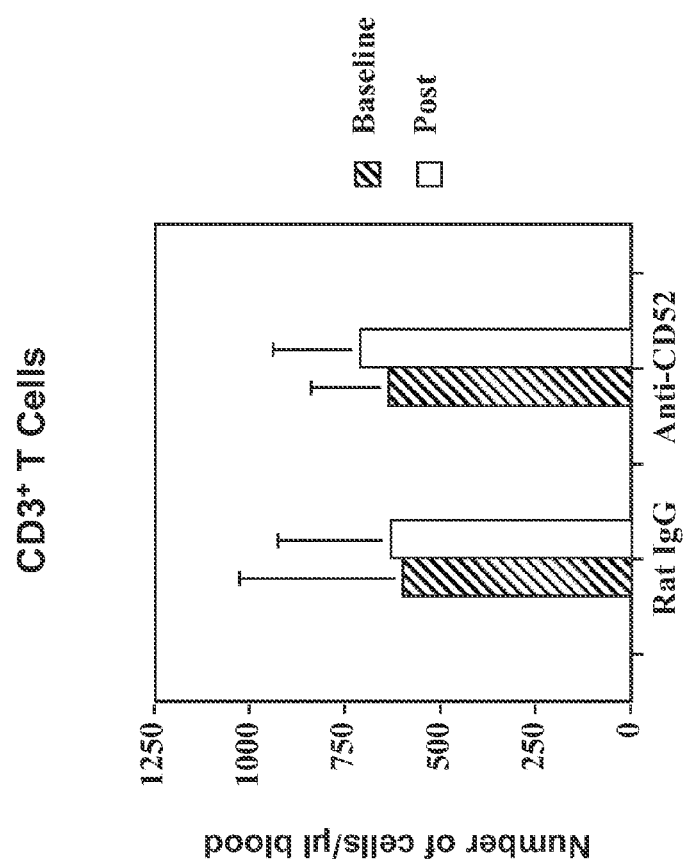
FIGS. 1A-1B show lack of lymphocyte depletion in NZB/NZWF1 mice treated with the monoclonal rat anti-mouse CD52 IgG2a antibody. Blood was collected from individual mice at baseline, prior to the first injection of control rat IgG or rat anti-mouse CD52 antibodies, and two days later, before the second injection of antibodies. Blood samples were stained and analyzed by flow cytometry to obtain absolute numbers of CD3+ T cells and CD19+ B cells.

This invention is based on our discoveries associated with administration of anti-CD52 antibodies to a subject. We have discovered that anti-CD52 antibodies increase infiltration of FoxP3$^+$ regulatory T cells to local inflammatory tissues (kidneys) in a mouse lupus model. We have also discovered that treatment with anti-CD52 antibodies can reduce urine protein and albumin levels in this mouse model.

Accordingly, this invention provides methods of treating lupus with anti-CD52 antibodies in a patient (e.g., a human patient). In some embodiments, the treatment will help recruit FoxP3+ regulatory T cells to local inflammatory tissues such as the CNS, kidneys, heart, and liver, thereby alleviating or preventing symptoms in lupus patients. In some embodiments, the treatment will help reduce urine protein and/or albumin levels in lupus patients. In some embodiments, the treatment will deplete lymphocytes in lupus patients. In further embodiments of this invention, the patient is also treated with an agent that stimulates growth and/or activation of FoxP3+ regulatory T cells, so as to improve regulation of the patient's immune system and alleviate symptoms of autoimmunity.

Manifestations of Lupus

The methods of this invention can be used in patients who suffer from the various manifestations of lupus including, without limitation, systemic lupus erythematosus; lupus nephritis; cutaneous lupus erythematosus; CNS lupus; cardiovascular, pulmonary, hepatic, haematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations. The methods of invention can be used to treat patients who are suffering an active lupus episode, or patients who have inactive lupus.

Anti-CD52 Antibody Therapies in the methods of this invention, antibodies to CD52 are administered to a patient in a therapeutically effective amount to reach clinical endpoints as measured by monitoring of an affected organ system (e.g., hematuria and/or proteinuria for lupus nephritis) and/or using a disease activity index that provides a composite score of disease severity across several organ systems (e.g., BRAG, SLAM, SLE-DAI, ECLAM). See, e.g., Mandl et al., "Monitoring patients with systemic lupus erythematosus" in *Systemic Lupus Erythematosus*, 4$^{th}$ edition, pp. 619-631, R. G. Lahita, Editor, Elsevier Academic Press, (2004). A therapeutically effective amount of anti-CD52 antibody is an amount that helps the treated subject to reach one or more desired clinical end points.

CD52 is a cell surface protein expressed at high levels by both normal and malignant B and T lymphocytes (Hale et al., *J Biol regul Homeost Agents* 15:386-391 (2001) Huh et al., *Blood* 92: Abstract 4199 (1998); Elsner et al., *Blood* 88:4684-4693 (1990; Gilleece et al., *Blood* 82:807-812 (1993); Rodig et al., *Clin Cancer Res* 12:7174-7179 (2006); Ginaldi et al., *Leuk Res* 22:185-191 (1998)). CD52 is expressed at lower levels by monocytes, macrophages, and eosinophils, with little expression found on mature natural killer (NK) cells, neutrophils, and hematological stem cells. Id. CD52 is also produced by epithelial cells in the epididymis and duct deferens, and is acquired by sperm during passage through the genital tract (Hale et al., 2001, supra; Domagala et al., *Med Sci Monit* 7:325-331 (2001)). The exact biological function of CD52 remains unclear but some evidence suggests that it may be involved in T cell migration and co-stimulation (Rowan et al., *Int Immunol* 7:69-77 (1995); Masuyama et al., *J Exp Med* 189:979-989 (1999); Watanabe et al., *Clin Immunol* 120:247-259 (2006)).

An example of a human CD52 antigen polypeptide sequence is:

(SEQ ID NO:1; NCBI Accession No. NP_001794)
MKRFLFLLLT ISLLVMVQIQ TGLSGQNDTS QTSSPSASSN

ISGGIFLFFV ANAIIHLFCF S

A mature human CD52 antigen is considerably shorter, having as few as 12 amino acids (Xia et al., *Eur J Immunol.* 21(7):1677-84 (1991)) and is glycosylated. For example, a mature human CD52 antigen may have this polypeptide sequence: GQNDTSQTSSPS (SEQ ID NO:2).

The anti-CD52 antibody therapies encompassed by this invention include any treatment regimens using an anti-CD52 antibody, including antibodies of any suitable isotype, such as IgG1, IgG2, IgG3, and IgG4. Useful antibodies also include those whose constant/Fc regions have been modified and bind to an Fc receptor on neutrophils and/or NK cells with the same or better affinity or otherwise have improved antibody-dependent cell-mediated cytotoxicity (ADCC) and complement-dependent cytotoxicity (CDC) functions. The anti-CD52 antibodies useful in this invention are those that bind specifically to a CD52, and do not bind specifically to non-CD52 molecules. Specific binding between an anti-CD52 antibody and CD52 can be determined, for example, by measuring $EC_{50}$ of the antibody's binding to CD52+ cells by flow cytometry. Specific binding can be indicated by an $EC_{50}$ range of, e.g., 0.5-10 μg/ml. For clinical applications, the anti-CD52 antibodies may preferably be monoclonal, with pharmaceutically acceptable purity. The antibodies may be administered in any suitable method, optionally with a pharmaceutically acceptable carrier, at a therapeutically effective amount, e.g., an amount that helps a patient to reach a desired clinical endpoint.

When a patient to be treated is a human, it is preferred that the anti-CD52 antibody binds specifically to human CD52. To minimize immunogenicity upon repeated administration to the human patient, it also may be preferred that the antibody is chimerized (e.g., a murine anti-CD52 antibody whose constant domains have been replaced with those of a human antibody), humanized (e.g., a human antibody whose CDRs have been replaced with those from a murine anti-human CD52 antibody), or fully human antibody. An example of useful antibodies are alemtuzumab (e.g., CAM-PATH-1H® and variants thereof). Alemtuzumab is a recombinant humanized IgG1 monoclonal antibody directed against human CD52 (hCD52), a 28 kD glycosylated glycosyl-phosphatidylinositol (GPI)-linked surface protein (Hale et al., *Tissue Antigens* 35:118-27 (1990); Hale et al., 2001, supra). Alemtuzumab is currently approved as a first line treatment against B-cell chronic lymphocytic leukemia and is in Phase III clinical trials for the treatment of multiple sclerosis. Useful antibodies include, without limitation, those that compete with alemtuzumab for binding to hCD52, and/or bind the same or an overlapping epitope as alemtuzumab or other epitopes on hCD52. For example, the humanized antibodies described in International Application PCT/US2010/034704 can be used.

Human anti-hCD52 antibodies can be made by those skilled in the art, using, for example, XENOMOUSE® technology (Amgen, Thousand Oaks, Calif.). Chimeric and humanized anti-hCD52 antibodies can be made with well established antibody technology from, for example, a rat anti-hCD52 antibody or a mouse anti-hCD52 antibody.

If desired, the anti-CD52 antibodies useful in this invention can comprise a detectable label to allow, e.g., monitoring in therapies, diagnosis, or assays. Suitable detectable labels include, for example, a radioisotope (e.g., as indium-111, Technetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group, or a chemiluminescent group. When labels are not employed, complex formation can be determined by surface plasmon resonance, ELISA, flow cytometry, or other suitable methods. Anti-CD52 antibodies used in this invention may be conjugated to another therapeutic agent, such as a bioactive compound (e.g., cytokines, and cytotoxic agents). Anti-CD52 antibodies used in the invention also may be conjugated, via, for example, chemical reactions or genetic modifications, to other moieties pegylation moieties) that improve the antibodies' pharmacokinetics such as half-life. In some embodiments, the anti-CD52 antibodies used in this invention can be linked to a suitable cytokine via, e.g., chemical conjugation or genetic modifications (e.g., appending the coding sequence of the cytokine in frame to an antibody coding sequence, thereby creating an antibody:cytokine fusion protein).

Increasing Infiltration of FoxP3+ Regulatory T Cells

We have discovered that anti-CD52 antibodies tend to increase FoxP3$^+$ regulatory T cells as compared to other T cells, including increasing the infiltration of these cells to local tissues, e.g., sites of inflammation or tissue damage. Regulatory T cells (also known as "Treg" or suppressor T cells) are cells that are capable of inhibiting the proliferation and/or function of other lymphoid cells via contact-dependent or contact-independent (e.g., cytokine production) mechanisms. Several types of regulatory T cells have been described, including γδ T cells, natural killer T (NKT) cells, CD8$^+$T cells, CD4$^+$T cells, and double negative CD4$^-$CD8$^-$T cells. See, e.g., Bach et al., *Immunol.* 3:189-98 (2003). CD4$^+$CD25$^+$FoxP3$^+$ regulatory T cells have been referred as "naturally occurring" regulatory cells; they express CD4, CD25 and forkhead family transcription factor FoxP3 (forkhead box p3).

An increase of Tregs may be desired for reducing symptoms of the autoimmune disease being treated. Thus, one can administer to a patient an agent that stimulates FoxP3$^+$ (e.g., CD4$^+$CD25$^+$FoxP3$^+$) regulatory T cells. The agent may, for example, activate those cells, expand the population of those cells, mobilize and increase circulation of those cells, and/or recruit those cells to target sites. Examples of such agents are rapamycin, active or latent TGF-β (e.g., TGF-β1, TGF-β2, TGF-β3, TGF-β4, and TGF-β5), IL-10, IL-4, IFN-α, vitamin D3, dexamethasone, and mycophenolate mofetil (see, e.g.; Barrat et al., *J. Exp. Med.* 195:603-616 (2002); Gregori et al., *J Immunol.* 167: 1945-1953 (2001); Battaglia et al., *Blood* 105: 4743-4748 (2005); Battaglia et al., *J. Immunol.* 177: 8338-8347 (2010)). In some embodiments of the invention, an increase of Tregs may occur at one or multiple sites of inflammation (e.g., blood, central nervous system, heart, live, joint, kidney, skin, intestinal tract, or vasculature).

The Treg-stimulatory agent may be administered before, during, or after treatment with an anti-CD52 antibody. Anti-CD52 antibodies used in this invention preferentially delete T effector cells and B cells, while preferentially sparing FoxP3$^+$ Tregs (See, e.g., Hu et al., *Immunology* 128: 260-270 (2009)). Thus, a therapeutic regimen that utilizes both an anti-CD52 antibody and a Treg-stimulating agent will greatly enhance the efficacy of lupus treatment, or treatment of other autoimmune diseases by re-equilibrating the patient's immune system.

Reducing Urine Protein and/or Albumin Level

A lupus patient may display proteinuria or albuminuria—an excess of serum protein or albumin in the urine. In lupus, renal damage, as measured by the levels of protein or albumin in the urine, is one of the most acute damages and accounts for at least 50% of the mortality. The treatment methods of this invention (with an anti-CD52 antibody alone or with a combination of an anti-CD52 antibody and a Treg-stimulating agent) can reduce the urine protein and/or albumin level of the patient by at least 25%, 50%, 75%, or 90%, as compared to the level prior to treatment. In some embodiments, the urine protein level prior to the administration of an anti-CD52 antibody is at least greater than or equal to 500 mg/L/day (e.g., 1,000 mg/L/day, 2,000 mg/L/day, 3,000 mg/L/day). After initial treatment with the anti-CD52 antibody, the urine protein level may be reduced to less than 500 mg/L/day or less than 1,000 mg/L/day.

Combination Therapy

In some aspects of this invention, an anti-CD52 antibody can be co-administered to a lupus patient with one or more additional therapeutic agents (e.g., an immunosuppressant) in a combination therapy. The second therapeutic agent can be, for example, a corticosteroid, a non-steroidal anti-inflammatory drug, a disease-modifying anti-rheumatic drugs (DMARDs) (e.g., cyclophosphamide or mycophenolic acid), an immunosuppressant (e.g., methotrexate and azathioprine), a molecule targeting B or T lymphocytes (e.g., a CD20 antibody, e.g., Rituximab, also known as Rituxan®, an anti-BLys antibody, or an anti-BAFF-R antibody). In some embodiments, the additional agent is, e.g., a cytokine (e.g., IL-7), an anti-cytokine receptor antibody, or a soluble receptor, that skews, manipulates, and/or augments the reconstitution process that occurs following lymphodepletion mediated by an anti-CD52 antibody (see, e.g., Sportes et al., *Cytokine Therapies: Ann. N.Y. Acad. Sci.* 1182:28-38 (2009)). The additional therapeutic agent(s) can be administered before, during or after the anti-CD52 antibody treatment.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

EXAMPLES

The following examples are meant to illustrate the methods and materials of the present invention. Suitable modifications and adaptations of the described conditions and parameters normally encountered in the art that are obvious to those skilled in the art are within the spirit and scope of the present invention.

Mouse Lupus Model

NZB/NZWF1 mice represent a spontaneous model of lupus. As they age, the animals develop autoantibodies against a variety of cellular antigens, ultimately leading to the deposition of immune complexes in the kidneys and progressively fatal renal disease (Peutz-Kootstra et al., *J Lab Clin Med* 137: 244-260 (2001)). In the following examples, we used NZB/NZWF1 female mice to study the effect of anti-CD52 antibodies on the course of systemic lupus.

Anti-CD52 Antibody

In Examples 1-6, a monoclonal rat anti-mouse CD52 IgG2a antibody was used. That rat isotype was not an optimal isotype for effector function (e.g., complement fixation and antibody-dependent cell-mediated cytotoxicity) in the mouse. In Examples 7-8, a monoclonal IgG2a mouse anti-mouse CD52 antibody was used.

In Examples 1-6, we divided NZB/NZWF1 mice (15 weeks old, Jackson Labs) into four groups and treated them with different test articles (Table 1). Cyclophosphamide, a nitrogen mustard alkylating agent, was used as a positive control in Examples 1-6. Cyclophosphamide has been used to treat various types of cancer and certain autoimmune disorders including lupus.

TABLE 1

| Treatment Group# | Test Articles | Dosage | Animals per group |
|---|---|---|---|
| 1 | PBS (Vehicle control) | Intraperitoneal injection: 400 µL | 5 |
| 2 | Normal rat IgG (Sigma) | Intraperitoneal injection: 400 µL of a 350 µg/mL stock solution (140 µg/mouse or ~3 mg/kg) | 10 |
| 3 | Monoclonal rat anti-mouse CD52 antibody | Intraperitoneal injection: 400 µL of a measured 350 µg/mL* stock solution (140 µg/mouse or ~3 mg/kg) | 9 |
| 4 | Cyclophosphamide | Intraperitoneal injection: 50 mg/kg in 200 µl saline weekly. Weigh mice to adjust dosage. | 5 |

*A rat IgG2a ELISA indicated that, of the total protein content in the stock solution, only 184 µg/ml consisted of rat IgG2a, suggesting that the effective dose may have been as low as 1.7 mg/kg.

Time points of Examples 1-6 are as follows:
i) Beginning at 19 weeks of age and every 4 weeks thereafter, blood was collected from individual mice for evaluation of IgG anti-double-stranded DNA (anti-dsDNA) antibody titers and a 24-hour urine collection was performed in metabolic cages for measurement of proteinuria and albuminuria.
ii) Treatment with test articles was initiated at 31 weeks of age when animals began developing significant titers of antibodies to dsDNA and/or elevated proteinuria. Group 2 treated with normal rat IgG and Group 3 treated with rat anti-mouse CD52 antibody received a total of two injections, respectively. Group 4 treated with cyclophosphamide received weekly injections until the end of the study,
iii) Prior to the first injection of antibodies, blood was collected from Group 2 and Group 3 for baseline fluorescence-activated cell sorting (FACS) analysis (staining for CD3, CD19 positive cells, absolute numbers of lymphocytes were counted.)
iv) Two days after the first injection of antibodies, a second injection of antibodies was given to Group 2 and Group 3. Prior to second injection, blood was collected from Group 2 and Group 3 for flow cytometry analysis (staining for CD3, CD19 positive cells, absolute counts were collected). Spleens from one mouse in Group 2 and one mouse in Group 3 were also collected for flow cytometry staining.

Any animals that became moribund during the course of the study were sacrificed, and one kidney was collected if possible. The study was terminated when the mice were 43 weeks of age and one kidney was collected from each animal for histology.

Example 1

Figure 1B:
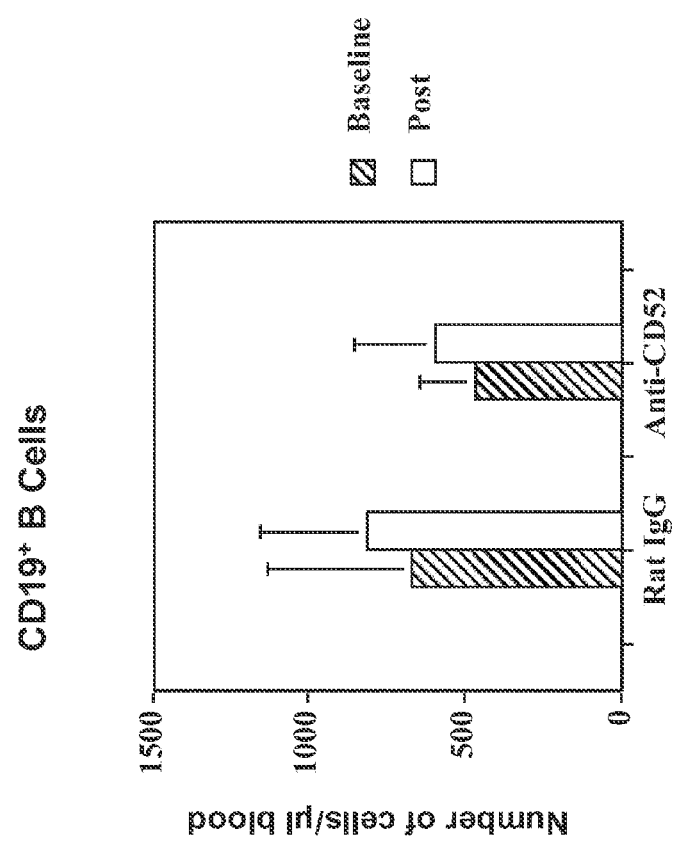

Lack of Lymphocyte Depletion NZB/NZWF1 Mice Treated with a Rat Anti-Mouse CD52 Antibody To determine whether treatment with the monoclonal rat anti-mouse CD52 antibody resulted in the depletion of $CD52^+$ lymphocytes, blood was collected from individual mice at baseline, prior to the first injection of rat IgG or rat anti-mouse CD52, and two days later, before the second injection of antibodies. Blood samples were stained and analyzed by flow cytometry to obtain absolute numbers of $CD3^+$ T cells and $CD19^+$ B cells. Samples of 50 µl of whole blood were blocked with 10% normal mouse serum and 0.05% sodium azide in RPMI medium and were then stained with rat anti-mouse CD3-APC and rat anti-mouse CD19-PE (BD Pharmingen, San Diego, Calif.). Lymphocytes were analyzed for staining on a FACSCalibur™ system (Becton-Dickinson, San Diego, Calif.). Data analysis was performed with Cell Quest Pro Software (Becton-Dickinson). The results indicated that there was no significant depletion of B or T lymphocytes (FIGS. 1A and 1B).

Example 2

Levels of Proteinuria and Albuminuria

A. Levels of Proteinuria

Figure 2A:
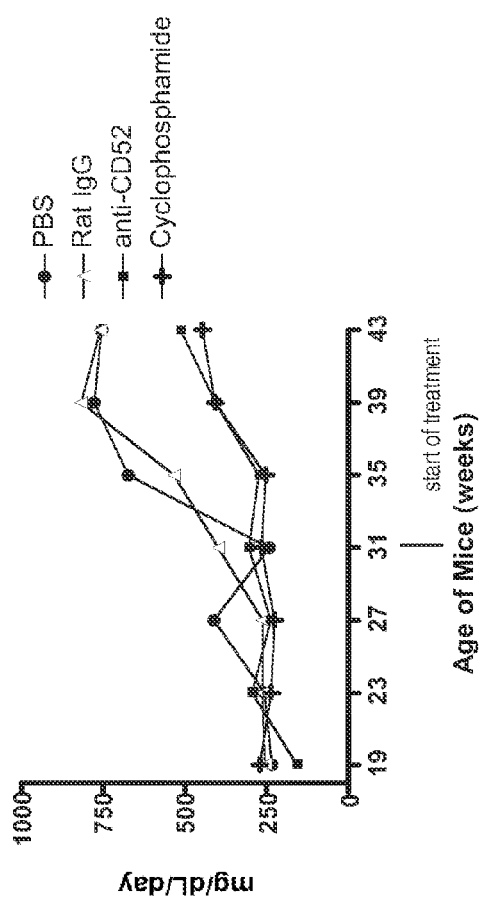
FIGS. 2A-2F show that treatment with the rat anti-mouse CD52 antibody successfully reduced urine protein levels in NZB/NZWF1 mice.
Figure 2B:
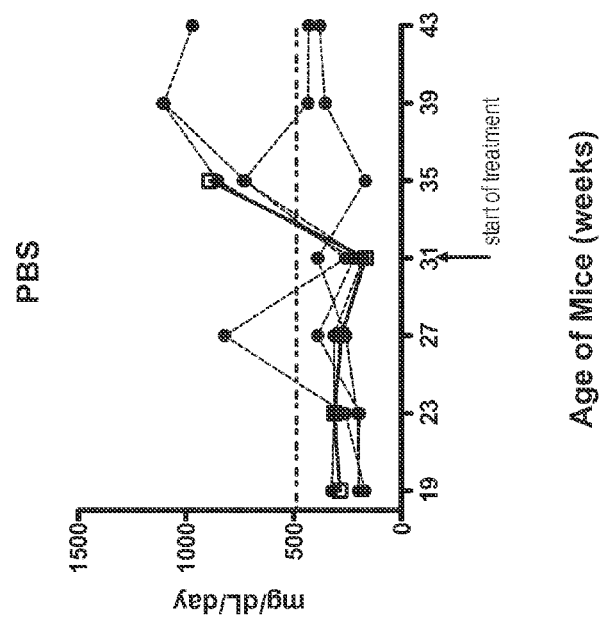
Figure 2C:
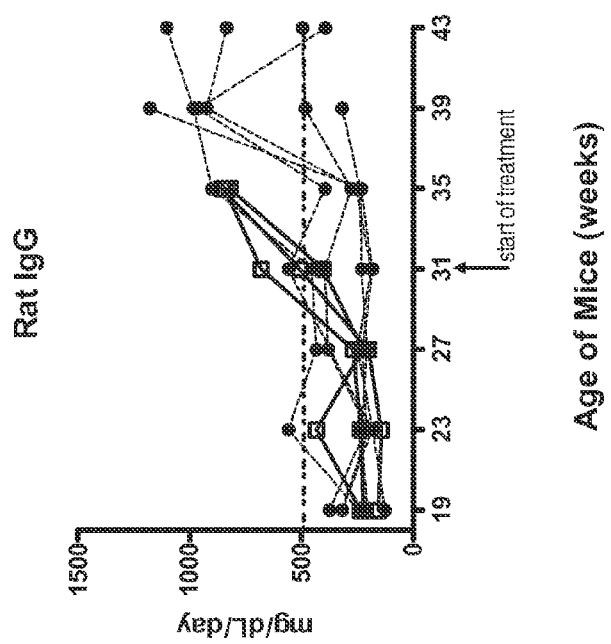
Figure 2D:
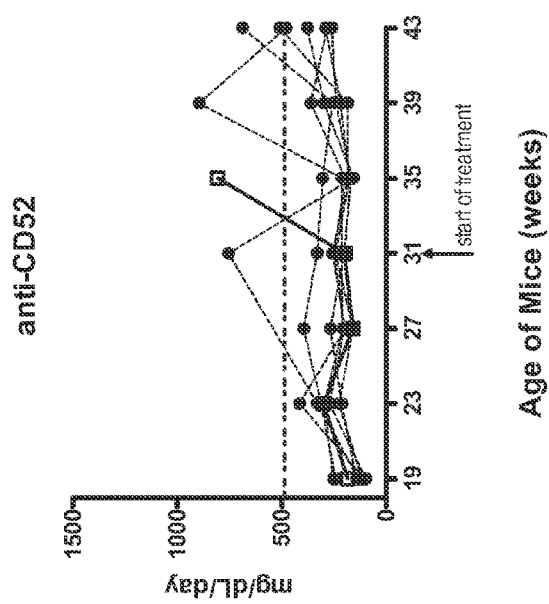
Figure 2E:
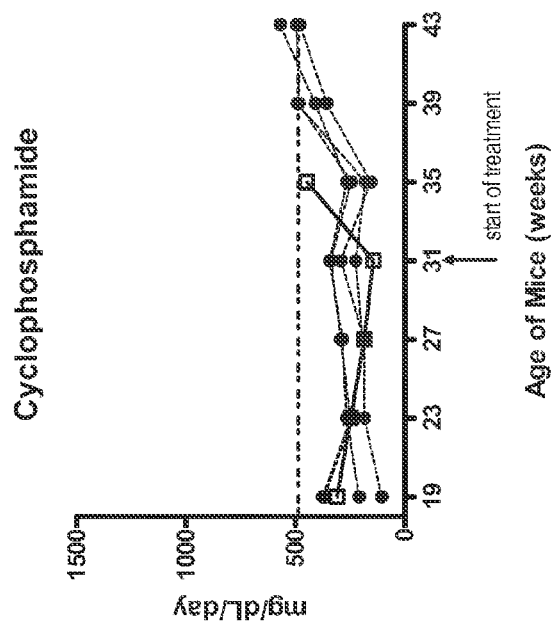
Figure 2F:
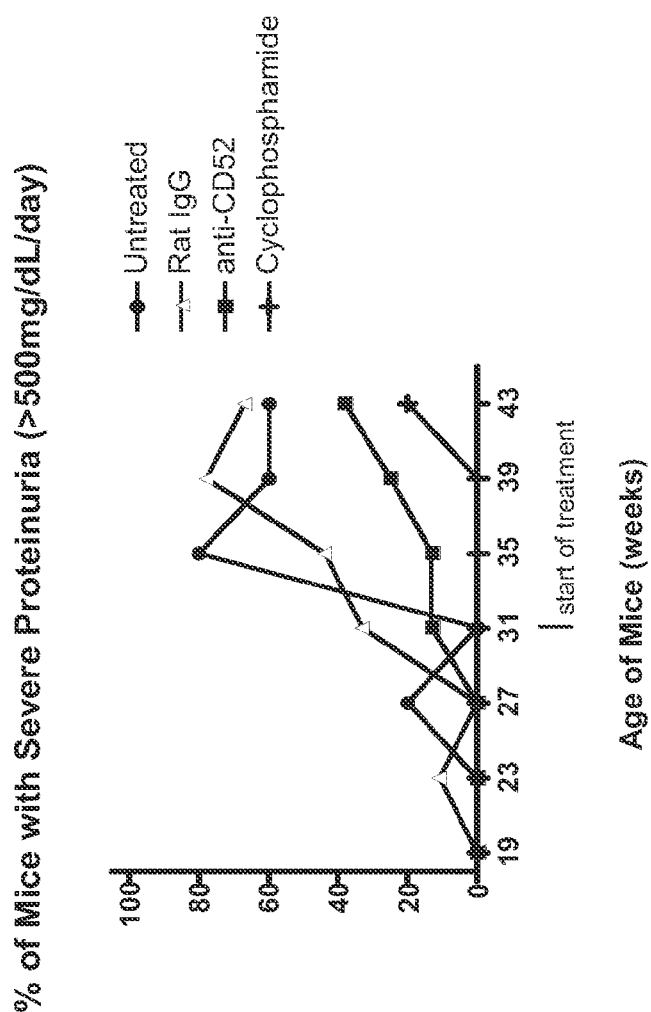

Levels of protein in the urine of individual mice were measured using a colorimetric assay designed to measure total protein concentration according to manufacturer's instructions (Microprotein-PR, Sigma). A reference standard was used to calculate the protein concentration of test samples. Despite the lack of lymphocyte depletion at the time of measurement, treatment with the rat anti-mouse CD52 antibody was successful in inhibiting the progression of renal disease as measured by total urine protein levels (FIGS. 2A-2E). Over the course of the study, anti-mouse CD52-treated mice displayed urine protein levels comparable to those of mice in the positive control cyclophosphamide-treated group, whereas control rat IgG-treated mice showed urine protein levels comparable to those of vehicle control mice (FIGS. 2A-2E). Only 38% of the anti-mouse CD52 antibody-treated mice and 20% of the cyclophosphamide-treated mice reached severe proteinuria (>500 mg/dL/day), compared to 67% of the rat IgG and 60% of the vehicle treated mice (FIG. 2F).

B. Levels of Albuminuria

Figure 3A:
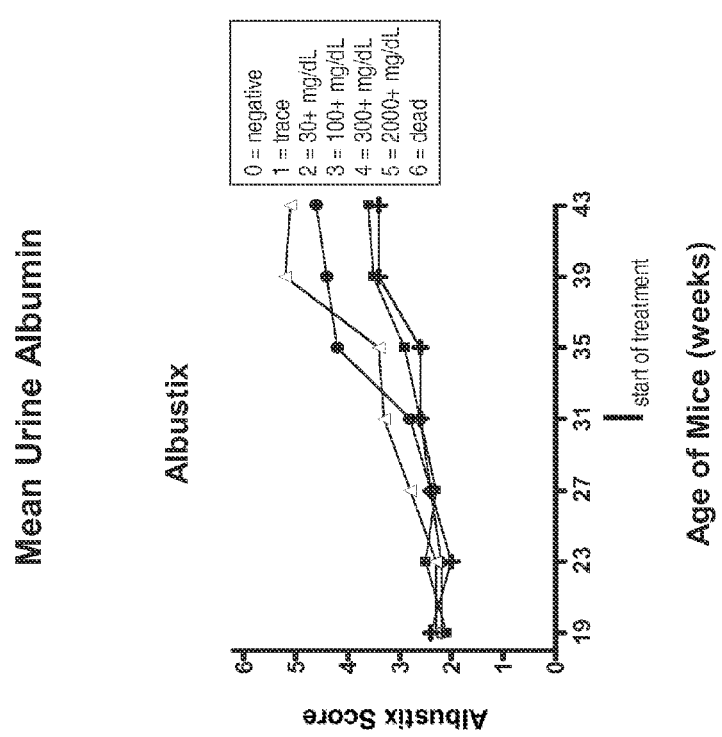
FIGS. 3A-3G show that treatment with the rat anti-mouse CD52 antibody successfully reduced urine albumin levels in NZB/NZWF1 mice. Levels of albumin in the urine were assessed with a semi-quantitative "Albustix" method (FIG. 3A), and a quantitative ELISA assay (FIG. 3B).
Figure 3B:
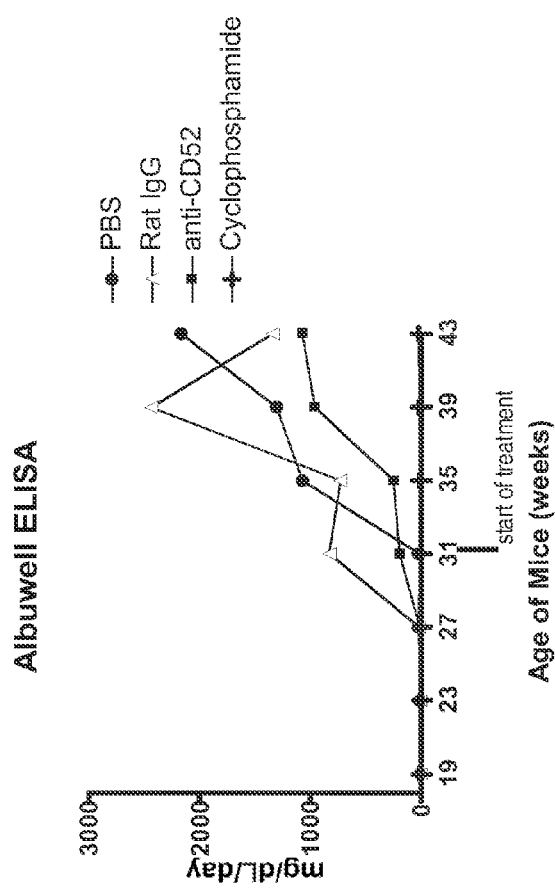
Figure 3C:
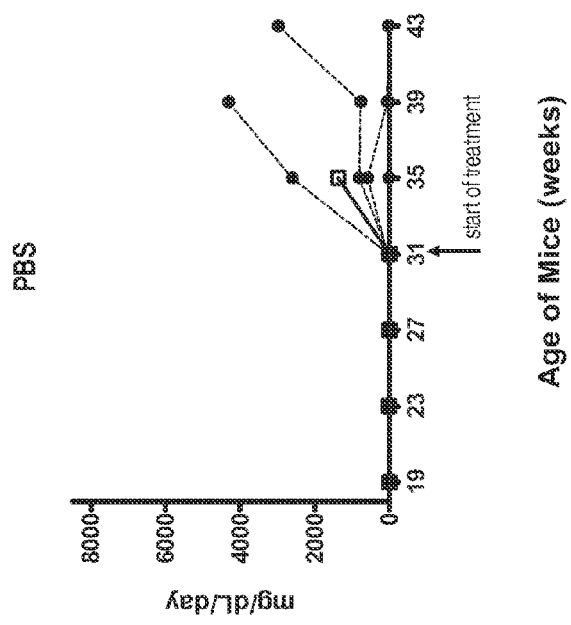
Figure 3D:
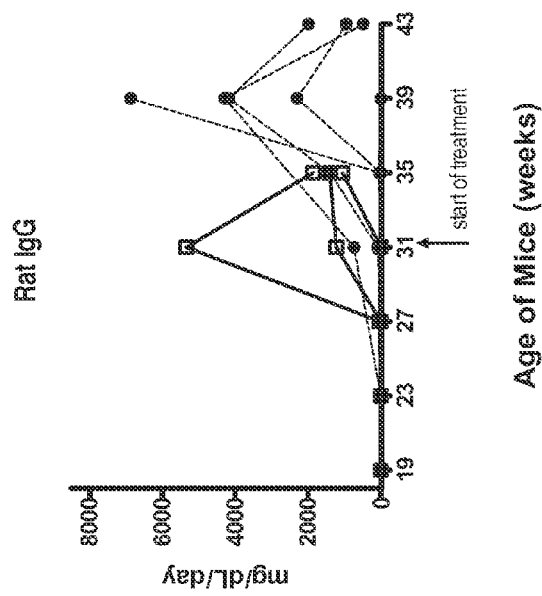
Figure 3E:
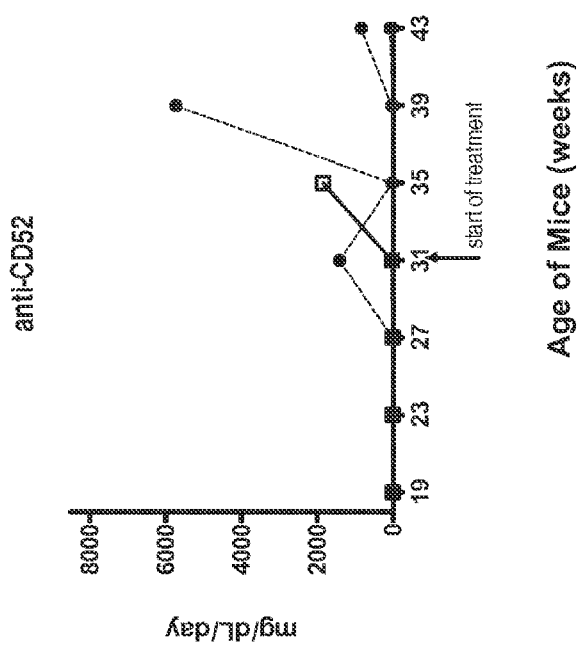
Figure 3F:
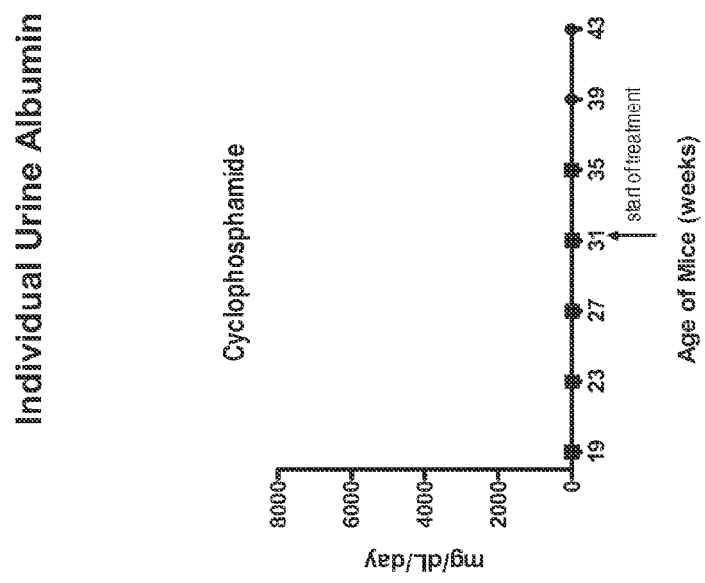
Figure 3G:
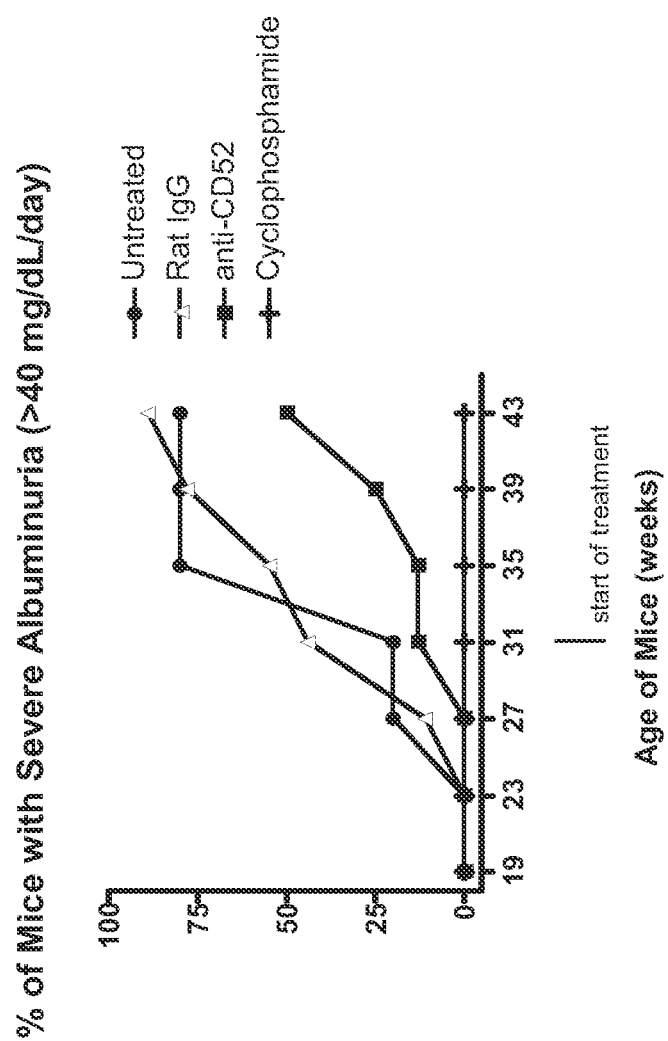

Levels of albumin in the urine were assessed using an indirect competitive ELISA kit according to manufacturer's instructions (Albuwell-M, Exocell, Inc.). The albumin concentration in the urine samples was derived from a standard curve obtained with known concentrations of murine albumin (FIG. 3B). A semi-quantitative "Albustix" method (Roche Diagnostics) (FIG. 3A) was also used, in which urine was deposited on an indicator filter paper that changes color according to the amount of albumin present in the urine and was then assigned a corresponding score of 0-6. In agreement with the total protein levels, treatment with anti-mouse CD52 antibody was also effective in inhibiting the development of albuminuria in NZB/NZWF1 mice (FIGS. 3A-3G). Urine albumin levels in the anti-CD52 antibody-treated mice were lower than those seen in the vehicle and rat IgG-treated mice. However, the suppression of albuminuria observed in this group was not as great as that obtained in the cyclophosphamide-treated group. Only 50% of the anti-CD52 antibody-treated mice developed significant albuminuria (>40 mg/dL/day) compared to 80% of the vehicle-treated and 89% of the rat IgG-treated mice by the end of the study (FIG. 3G).

Example 3

Levels of Antibodies to Double-Stranded DNA

Figure 4:
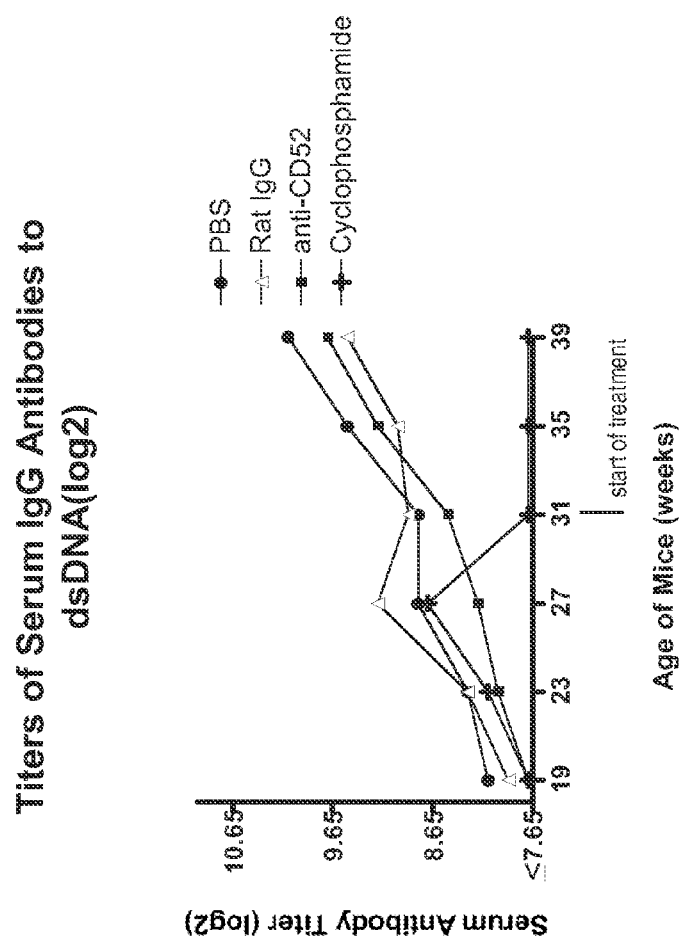
FIG. 4 shows that treatment with the rat anti-mouse CD52 antibody had no detectable effect on the development of autoantibodies against dsDNA. Antibody titers of mice treated with anti-mouse CD52 were comparable to the titers of the vehicle and rat IgG-treated mice. Only cyclophosphamide treatment effectively reduced the rise in serum antibodies to dsDNA.

Titers of IgG antibodies to dsDNA in serum samples from individual mice were measured by ELISA. Mouse dsDNA (The Jackson Laboratory, Bar Harbor, Me.) was digested with S1 nuclease (Invitrogen, Carlsbad, Calif.) to remove any ssDNA and was then used to coat the wells of a 96-well ELISA plate (100 µl/well of 1 µg/ml dsDNA) overnight at 4° C. The plates were pre-treated with 0.01% protamine sulphate in water to facilitate adhesion of the DNA. After coating, the plates were incubated with 2.5% bovine serum albumin blocking buffer for 1 hour at 37° C. and washed. 100 µl of serial 2-fold dilutions of serum were then added to duplicate wells and incubated at 37° C. for 1 hour. The plates were washed and horseradish peroxidase (HRP)-conjugated goat anti-mouse IgG (Pierce, Rockford, Ill.) was added to detect antibodies bound to dsDNA (37° C. for 1 hour). After washing, HRP substrate was added, and the optical density (OD) of the colorimetric product was read at 490 nM with a reference wavelength of 650 nM on a dual wavelength plate reader (Molecular Devices, Sunnyvale, Calif.). The antibody titre was defined as the reciprocal of the dilution of serum giving an OD greater than or equal to 0.1. Normal mouse serum was used as a negative control (titer≤200, the lowest dilution tested), and pooled serum from aged lupus mice was used as a positive control (titer of 25,600). Treatment with the rat anti-mouse CD52 antibody had no detectable effect on the development of autoantibodies against dsDNA (FIG. 4). Antibody titers of mice treated with anti-mouse CD52 were comparable to the titers of the vehicle and rat IgG-treated mice. Only cyclophosphamide treatment effectively reduced the rise in serum antibodies to dsDNA (FIG. 4).

Example 4

Improvement in Survival

Figure 5:
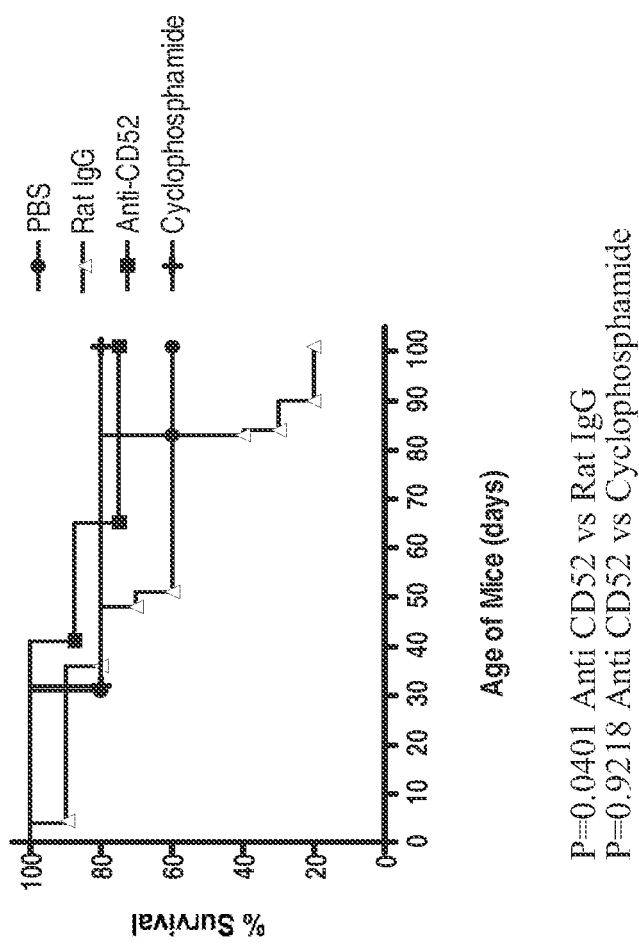
FIG. 5 shows that treatment with the rat anti-mouse CD52 antibody provided a significant survival benefit in NZB/NZWF1 mice. Comparable levels of survival were obtained with two doses of anti-mouse CD52 antibody (75% survival) versus weekly injections of cyclophosphamide (80%) (P value=0.9218, anti-mouse CD52 antibody vs. cyclophosphamide). Survival was only 20% in mice treated with control rat IgG (P value=0.0401, anti-mouse CD52 antibody vs. control rat IgG) (FIG. 5).

Treatment with the rat anti-mouse CD52 antibody was well tolerated in NZB/NZWF1 mice. Comparable levels of survival were obtained with two doses of anti-mouse CD52 antibody (75% survival) versus weekly injections of cyclophosphamide (80% survival) (P value=0.9218, anti-mouse CD52 antibody vs. cyclophosphamide) (FIG. 5). Survival was only 20% in mice treated with control rat IgG (P value=0.0401, anti-mouse CD52 antibody vs. control rat IgG) (FIG. 5). By comparison, vehicle-treated mice showed a 60% survival rate (FIG. 5), suggesting that the injection of a large amount of immunoglobulin protein in the control rat IgG group may have worsened disease, perhaps by stressing the kidneys, while the same amount of anti-mouse CD52 material provided a therapeutic benefit.

Example 5

Histological Examination of Kidneys

Kidneys were collected at sacrifice, fixed in 10% neutral buffered formalin then embedded in paraffin. Sections were cut to a thickness of 5 μm and stained with hematoxylin and eosin (ME), phosphotungistic acid hematoxylin (PTAH) and periodic acid Schiff (PAS) stains. Several animals in the negative control groups (vehicle and rat IgG) had to be sacrificed or were found dead during the course of the study. As a result, few kidneys were available for analysis at the end of the study thus limiting statistical power.

Figure 6A:
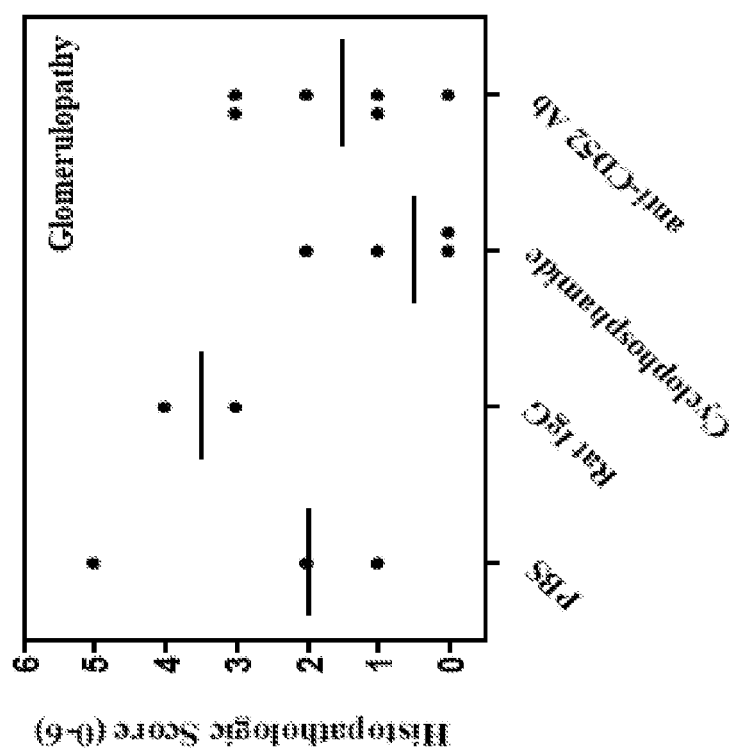
FIGS. 6A-6C show the histological examination results of the collected mouse kidneys. Although there were no statistically significant differences in median glomerulopathy, interstitial inflammation or protein casts severity scores between the treatment groups, treatment with the anti-mouse CD52 antibody and cyclophosphamide reduced the median glomerulopathy scores compared to the rat IgG and vehicle control groups as shown in FIG. 6A. Reduced interstitial inflammation was also observed in the cyclophosphamide treated group as shown in FIG. 6B.
Figure 6B:
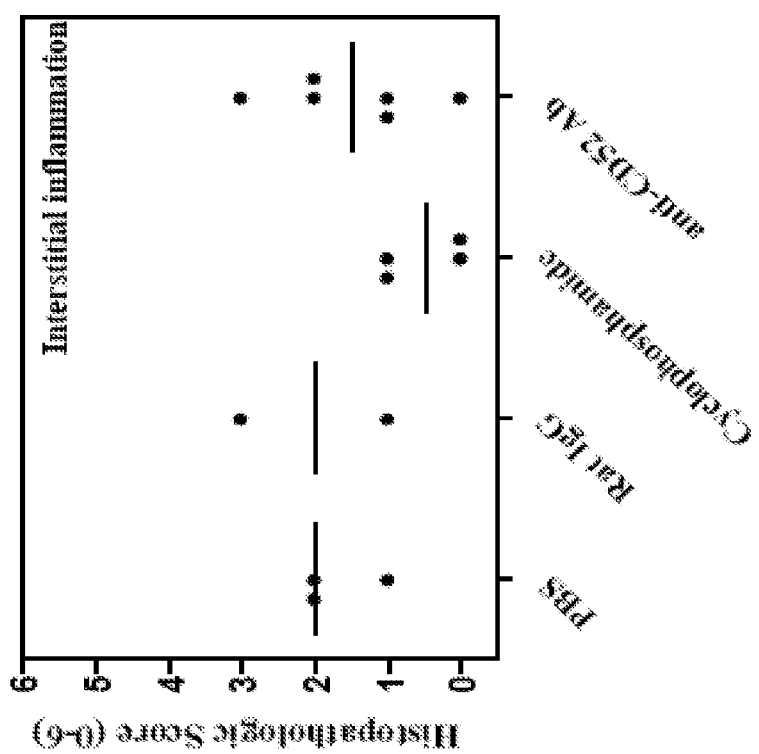
Figure 6C:
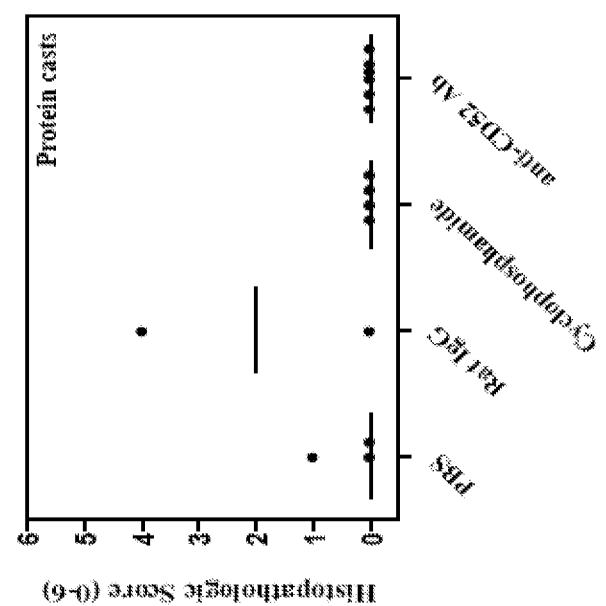

The collected kidneys were further examined. There were no statistically significant differences in median glomerulopathy, interstitial inflammation or protein casts severity scores between the treatment groups (FIGS. 6A-6C). However, certain trends were apparent. Treatment with the anti-mouse CD52 antibody and cyclophosphamide reduced the median glomerulopathy scores compared to the rat IgG and vehicle control groups (FIG. 6A). Reduced interstitial inflammation was also observed in the cyclophosphamide treated group (FIG. 6B).

Example 6

Increased FoxP3$^+$ Regulatory T Cells in Kidneys

Figure 7A:
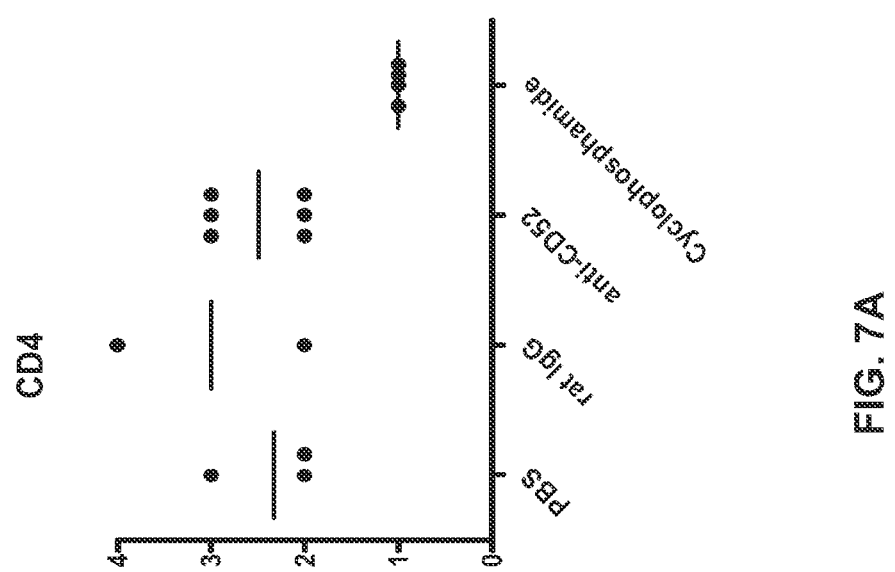
FIGS. 7A-7C show an increase in FoxP3$^+$ regulatory T cells infiltrating the kidneys. Mice kidneys were stained for the presence of CD4$^+$, CD8$^+$, and FoxP3$^+$ cells using immunofluorescently tagged antibodies. Kidney sections were scored blindly on a scale of 0-4 for the relative abundance of positive cells. Cyclophosphamide treatment resulted in a significant decrease in CD4$^+$, CD8$^+$, and FoxP3$^+$ cells infiltrating the kidneys. By comparison, treatment with anti-CD52 antibody failed to prevent infiltration of the kidneys by CD4$^+$ and CD8$^+$ lymphocytes, but increased the presence of cells positive for FoxP3, a marker for regulatory T cells.
Figure 7B:
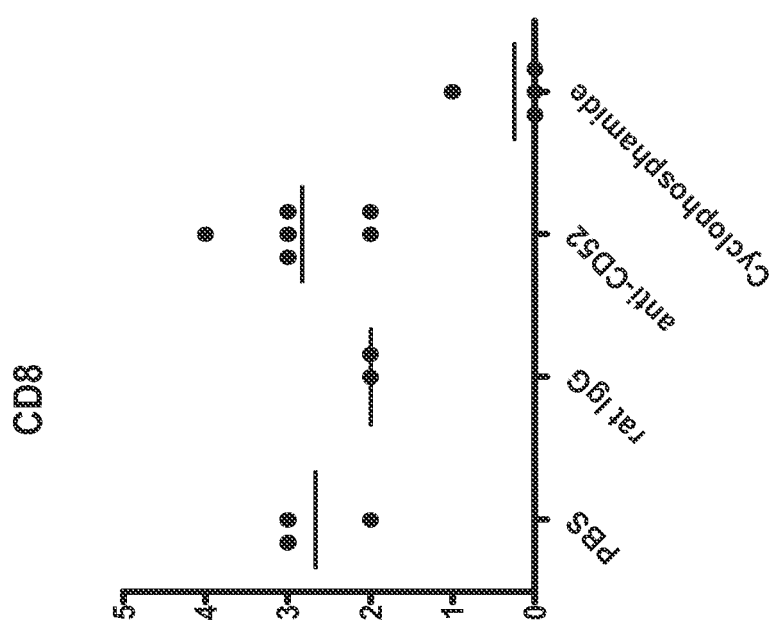
Figure 7C:
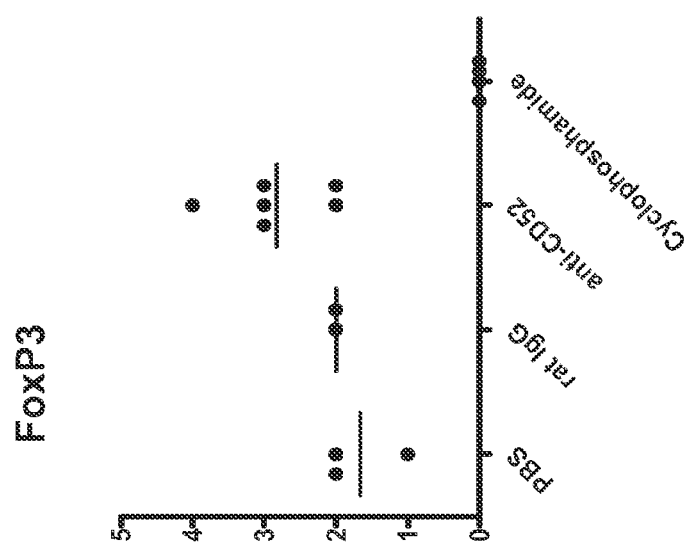

Kidney sections, obtained in Example 5, were further stained for the presence of CD4$^+$, CD8$^+$, and FoxP3$^+$ cells using immunofluorescently tagged antibodies. For the staining of CD4 and CD8 positive cells, kidney frozen sections were fixed with acetone, incubated sequentially with peroxidase (Dako), avidin, biotin (Biocare) and protein (Dako) blocks followed by biotinylated rat anti-mouse CD4 (clone L3T4; BD Pharmingen) or biotinylated goat anti-mouse CD8 (clone Ly-2; BD Pharmingen), streptavidin-HRP and DAB (3-3'-diaminobenzidine) to produce a brown staining on positive cells. For the staining of FoxP3 positive cells, kidney frozen sections were fixed with 10% neutral buffered formalin and incubated sequentially with peroxidase and protein blocks. A rat anti-mouse FoxP3 antibody was then added (eBioscience) followed by Mach-2 HRP-conjugated anti-rabbit antibody (Biocare) and DAB to produce a brown staining on positive cells. All sections were then also stained with hematoxylin to visualize cells. The sections were scored blindly on a scale of 0-4 for the relative abundance of positive cells. Cyclophosphamide treatment resulted in a significant decrease in CD4$^+$, CD8$^+$, and FoxP3$^+$ cells infiltrating the kidneys (FIGS. 7A-7C). By comparison, treatment with anti-CD52 antibody failed to prevent infiltration of the kidneys by CD4$^+$ and CD8$^+$ lymphocytes, but increased the presence of cells positive for FoxP3, a marker for regulatory T cells (FIGS. 7A-7C).

Example 7

Figure 8A:
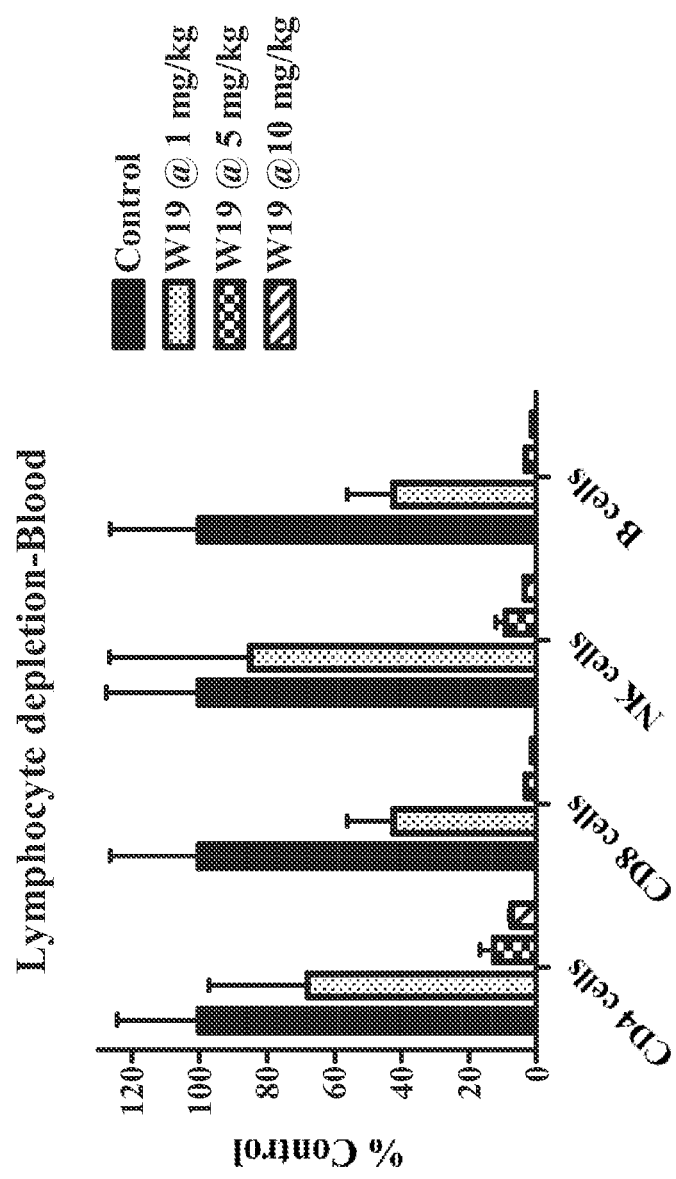
FIGS. 8A-8B show effective lymphocyte depletion by a monoclonal mouse anti-mouse CD52 antibody (clone W19) in NZB/NZWF1 mice at different dose levels 5 mg/kg and 10 mg/kg). In the blood (FIG. 8A), dose-dependent depletion was observed in all lymphoid populations with the 5 m/kg and 10 mg/kg doses, resulting in nearly complete depletion of all cell types (CD4$^+$ cells, CD8$^+$ cells, NK cells and B cells). In the spleen (FIG. 8B), similar dose-dependent depletion was observed. In particular, significant depletion of both CD4$^+$ and CD8$^+$ T cells was observed in the spleen, while B cells appear to be depleted to a lesser extent at all the dosage levels examined.
Figure 8B:
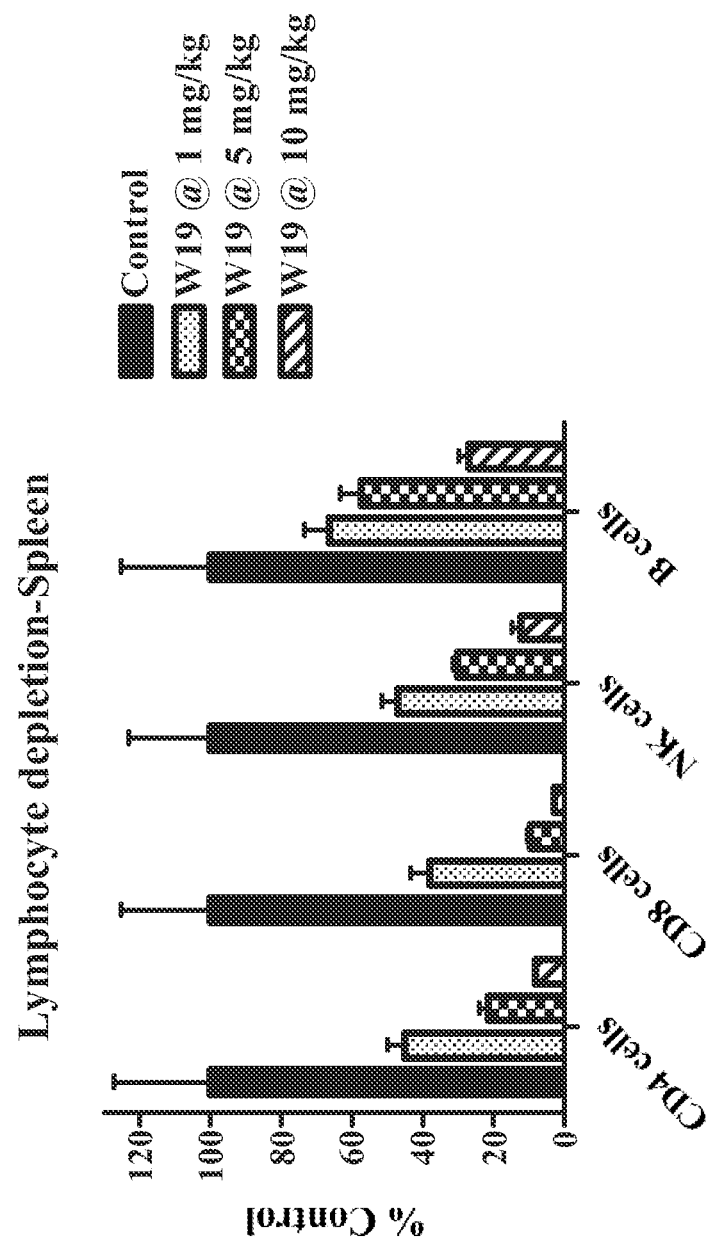

Lymphocyte Depletion in NZB/NZWF1 Mice Treated with a Monoclonal Mouse Anti-Mouse CD52 Antibody A depletion experiment was conducted to determine whether lupus mice are susceptible to lymphocyte depletion through targeting mouse CD52 using a monoclonal IgG2a mouse anti-mouse CD52 antibody generated in-house (clone W19). NZB/NZWF1 mice were treated with vehicle, 1 mg/kg, 5 mg/kg, or 10 mg/kg of the monoclonal mouse anti-mouse CD52 antibody. Three days following the treatment, splenocytes and peripheral blood were collected, and the extent of lymphocyte depletion was evaluated using flow cytometry. Significant level of lymphocyte depletion was observed in both the blood and the spleen at all dose levels of antibody. In the blood (FIG. 8A), dose-dependent depletion was observed in all lymphoid populations with the 5 and 10 mg/kg doses resulting in nearly complete depletion of all cell types. Similar dose-dependent depletion was also observed in the spleen (FIG. 5B). While significant depletion of both CD4$^+$ and CD8$^+$ T cells was observed in the spleen, B cells appeared to be depleted to a lesser extent at all dose levels examined.

Example 8

Analysis of the Efficacy of an Anti-Mouse CD52 Antibody in NZB/NZW Female Mice The monoclonal anti-mouse CD52 antibody, used in Example 7, is further tested for its impact on the development and/or progression of disease in the NZB/NZWF1 mouse lupus model. First, groups of ten mice receive two injections of a control antibody or the monoclonal mouse anti-mouse CD52 antibody at 10 mg/kg, one week apart prior to the development of overt disease, at approximately 21 weeks of age. Then separate groups of ten mice receive two injections of a control antibody or a monoclonal mouse anti-mouse CD52 antibody at 10 mg/kg, one week apart during the course of disease, at approximately 32 weeks of age. A positive control group receives cyclophosphamide at 50 mg/kg weekly starting at approximately 21 weeks of age. We examine the following readouts: 1) lymphocyte depletion measured by flow cytometry; 2) development of autoantibodies to dsDNA measured by ELISA; 3) proteinuria; and 4) histological analysis of the kidneys; and further determine the extent to which targeting CD52 in this manner mitigates kidney damage.

---

What is claimed is:

1. A method of increasing FoxP3+ regulatory T cells in a patient with lupus, comprising
   selecting a patient for treatment for lupus, and
   administering to the patient in vivo antibody therapy consisting of administration of an anti-CD52 monoclonal antibody, wherein the anti-CD52 monoclonal antibody increases FoxP3+ regulatory T cells in the patient,
   wherein the method does not include ex vivo expansion of T cells to produce regulatory T cells,
   thereby treating lupus in the patient.

2. The method of claim 1, wherein the method further comprises administering to the patient an agent that stimulates said regulatory T cells.

3. The method of claim 2, wherein the agent is rapamycin, a TGF-β, IL-10, IL-4, IFN-α, vitamin D3, dexamethasone, or mycophenolate mofetil.

4. The method of claim 3, wherein the TGF-β is an active or latent form of any one of TGF-β1, TGF-β2, TGF-β3, TGF-β4, and TGF-β5.

5. The method of claim 1, wherein said regulatory T cells are increased at least at one site of inflammation.

6. The method of claim 5, wherein the site of inflammation is blood, central nervous system (CNS), heart, liver, joint, kidney, lung, skin, intestinal tract, or vasculature.

7. The method of claim 1, wherein the anti-CD52 monoclonal antibody reduces the level of urine protein, or urine albumin, or both, in the patient.

8. The method of claim 7, wherein the patient is a human.

9. The method of claim 7, wherein the anti-CD52 monoclonal antibody is a humanized or human anti-CD52 monoclonal antibody.

10. The method of claim 9, wherein the antibody is alemtuzumab.

11. The method of claim 1, wherein the patient is a human.

12. The method of claim 1, wherein the anti-CD52 monoclonal antibody is a humanized or human anti-human CD52 monoclonal antibody.

13. The method of claim 12, wherein the antibody is alemtuzumab.

14. The method of claim 1, wherein the anti-CD52 monoclonal antibody is administered in a monotherapy.

15. The method of claim 14, wherein said regulatory T cells are increased at least at one site of inflammation.

16. The method of claim 14, wherein the patient is a human and wherein the anti-CD52 monoclonal antibody is a humanized or human anti-human CD52 monoclonal antibody.

17. The method of claim 16, wherein the antibody is alemtuzumab.

* * * * *

SEQUENCE LISTING

<160> NUMBER OF SEQ ID NOS: 2

<210> SEQ ID NO 1
<211> LENGTH: 61
<212> TYPE: PRT
<213> ORGANISM: Homo sapiens

<400> SEQUENCE: 1

```
Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60

<210> SEQ ID NO 2
<211> LENGTH: 12
<212> TYPE: PRT
<213> ORGANISM: Homo sapiens

<400> SEQUENCE: 2

Gly Gln Asn Asp Thr Ser Gln Thr Ser Ser Pro Ser
1               5                   10
```